US007179623B2

(12) United States Patent
Livshits et al.

(10) Patent No.: US 7,179,623 B2
(45) Date of Patent: Feb. 20, 2007

(54) METHOD OF PRODUCING AMINO ACIDS USING *E. COLI* TRANSFORMED WITH SUCROSE PTS GENES

(75) Inventors: Vitaliy Arkadyevich Livshits, Moscow (RU); Vera Georgievna Doroshenko, Moscow (RU); Sergei Vladimirovich Mashko, Moscow (RU); Valery Zavenovich Akhverdian, Moscow (RU); Yury Ivanovich Kozlov, Moscow (RU)

(73) Assignee: Ajinomoto Co., Inc., Tokyo (JP)

( * ) Notice: Subject to any disclaimer, the term of this patent is extended or adjusted under 35 U.S.C. 154(b) by 0 days.

(21) Appl. No.: 11/204,011

(22) Filed: Aug. 16, 2005

(65) Prior Publication Data
US 2006/0030009 A1 Feb. 9, 2006

Related U.S. Application Data

(62) Division of application No. 09/841,609, filed on Apr. 25, 2001, now Pat. No. 6,960,455.

(30) Foreign Application Priority Data
Apr. 26, 2000 (RU) .............................. 2000110350

(51) Int. Cl.
C12P 13/04 (2006.01)
C12N 9/00 (2006.01)
C12N 1/20 (2006.01)
C07K 1/00 (2006.01)
C07H 21/04 (2006.01)

(52) U.S. Cl. .............. 435/106; 435/108; 435/115; 435/116; 435/183; 435/194; 435/252.33; 530/350; 536/23.2

(58) Field of Classification Search ................ 435/183, 435/194, 252.33, 106, 108, 115, 116; 530/350; 536/23.2
See application file for complete search history.

(56) References Cited

U.S. PATENT DOCUMENTS

| 4,346,170 | A | 8/1982 | Sano et al. |
| 5,175,107 | A | 12/1992 | Debabov et al. |
| 5,534,421 | A | 7/1996 | Livshits et al. |
| 5,538,873 | A | 7/1996 | Debabov et al. |
| 5,631,157 | A | 5/1997 | Debabov et al. |
| 5,658,766 | A | 8/1997 | Livshits et al. |
| 5,705,371 | A | 1/1998 | Debabov et al. |
| 5,976,843 | A | 11/1999 | Debabov et al. |
| 6,132,999 | A | 10/2000 | Debabov et al. |
| 6,165,756 | A | 12/2000 | Debabov et al. |
| 6,297,031 | B1 | 10/2001 | Debabov et al. |
| 6,303,348 | B1 | 10/2001 | Livshits et al. |
| 6,653,111 | B2 | 11/2003 | Debabov et al. |
| 6,737,255 | B2 | 5/2004 | Livshits et al. |
| 6,887,691 | B2 | 5/2005 | Livshits et al. |
| 2001/0049126 | A1 | 12/2001 | Livshits et al. |
| 2002/0058314 | A1 | 5/2002 | Livshits et al. |
| 2003/0148473 | A1 | 8/2003 | Livshits et al. |
| 2004/0038380 | A1 | 2/2004 | Debabov et al. |
| 2004/0132165 | A1 | 7/2004 | Akhverdian et al. |
| 2004/0229320 | A1 | 11/2004 | Stoynova et al. |
| 2004/0229321 | A1 | 11/2004 | Savrasava et al. |
| 2005/0048631 | A1 | 3/2005 | Klyachko et al. |
| 2005/0054061 | A1 | 3/2005 | Klyachko et al. |
| 2005/0124048 | A1 | 6/2005 | Akhverdian et al. |
| 2005/0176033 | A1 | 8/2005 | Klyachko et al. |
| 2005/0191684 | A1 | 9/2005 | Zimenkov et al. |
| 2005/0202543 | A1 | 9/2005 | Livshits et al. |
| 2005/0214911 | A1 | 9/2005 | Marchenko et al. |
| 2005/0214913 | A1 | 9/2005 | Marchenko et al. |

FOREIGN PATENT DOCUMENTS

EP 0 519 113 12/1992

OTHER PUBLICATIONS

Bockmann, J., et al., "Characterization of a Chromosomally Encoded, Non-PTS Metabolic Pathway for Sucrose Utilization in *Escherchia coli* EC3132," Mol. And General Genetics 1992;235(1):22-32.
Burkovski et al., "Bacterial amino acid transport proteins: occurrence, functions, and significance for biotechnological application," Appl. Microbiol. Biotechnol. 2002;58(3):265-274.
Debabov, V., et al., "Construction of strains producing L-threonine," Proceedings of the IVTH International Symposium on Genetics of Industrial Microorganisms, 1982, pp. 254-258.
Derwent Abstract of Research Disclosure, AN 2000-439902 (38), vol. 433, No. 020, 2 pp, "Fermentative Production of Amino Acids and Vitamins, Useful e.g. in Medicine, by Growing *Escherichia coli* that includes the Chromosomally Coded Sucrose System," May 10, 2000.
Garcia, J. L., et al., "Colning in *Escherichia coli* and Molecular Analysis of the Sucrose System of the Salmonella Plasmid SCR-53," Mol. & General Genetics 1985;201(3):575-577.
Jacobson, G.R., "Carbohydrate uptake in the oral pathogen *Streptococcus mutans:* mechanisms and regulation by protein phosphorylation," Biochimie 1989;71:997-1004.
Keevil, C.W., et al., "Evidence that Glucose and Sucrose Uptake in Oral Streptococcal Bacteria Involves Independent Phosphotransferase and Proton-Motive Force-Mediated Mechanisms," Archs. Oral Biol. 1984;29(11):871-878.

(Continued)

Primary Examiner—Tekchand Saidha
Assistant Examiner—Christian L. Fonda
(74) Attorney, Agent, or Firm—Cermak & Kenealy, LLP; Shelly Guest Cermak

(57) ABSTRACT

Amino acids such as threonine, homoserine, isoleucine, lysine, valine and tryptophan are produced using a bacterium belonging to the genus *Escherichia* which has been constructed from a sucrose non-assimilative strain belonging to the genus *Escherichia* and which harbors sucrose non-PTS or PTS genes and has an ability to produce the amino acid.

3 Claims, 4 Drawing Sheets

OTHER PUBLICATIONS

Sahin-Töth, M., et al., "Cloning, sequencing, expression of cscA invertase from *Escherichia coli* B-62," Can. J. Microbiol, 1999;45:418-422.

Schmid, K., et al., "Plasmid-Mediated Sucrose Metabolism in *Escherichia coli* K12: Mapping of the scr Genes of pUR4000," Mol. Microbiol, 1988;2(1):1-8.

Slee, A. M., et al., "Sucrose Transport by *Streptococcus mutans* Evidence for Multiple Transport Systems," Biochimica et Biophysuca Acta 1983;692:415-424.

Tsunekawa, H., et al., "Acquisition of Sucrose Utilization System in *Escherichia coli* K-12 Derivatives and Its Applications to Industry," Appl. Environ. Microbiol. 1992;58(6):2081-2088.

METHOD OF PRODUCING AMINO ACIDS USING E. COLI TRANSFORMED WITH SUCROSE PTS GENES

This application claims the benefit of U.S. patent application Ser. No. 09/841,609 filed on Apr. 25, 2001, now U.S. Pat. No. 6,960,455, as a divisional under 35 U.S.C. §120, which is incorporated by reference in its entirety.

BACKGROUND OF THE INVENTION

1. Field of the Invention

The present invention relates to biotechnology and, more specifically, to a method for producing amino acids by fermentation using an amino acid-producing bacterium belonging to the genus *Escherichia*, which is capable of utilizing sucrose as the sole carbon source.

2. Description of the Related Art

Sucrose and sucrose-containing substrates (e.g. molasses) are often used as a starting point for the microbial production of commercial products such as amino acids, vitamins and organic acids. The process for production of amino acids from carbohydrates strives to maximize the efficiency of converting the carbon skeleton of a carbohydrate into a desired product.

The majority of sucrose-positive bacteria take up and phosphorylate sucrose by a phosphoenol pyruvate-dependent, sucrose-6-phosphotransferase system (sucrose PTS) to yield intracellular sucrose-6-phosphate. This phosphate is hydrolyzed by a sucrose-6-phosphate hydrolase (invertase or sucrase) into D-glucose 6-phosphate and D-fructose, which is itself phosphorylated by an ATP-D-fructose-6-phosphate phosphotransferase (fructokinase). Such systems and metabolic pathways have been described at the molecular level for the gram-positive bacteria *Bacillus subtilis* and *Streptococcus mutans* (Debarbouille et al., 1991. Res. Microbiol., 142: 757–764; Sato et al., 1989. J. Bacteriol., 171: 263–271) and for gram-negative bacteria. Furthermore, a plasmid-coded pUR400 system from enteric bacteria has been reported (Aulkemeyer et al., (1991) Mol. Microbiol., 5: 2913–2922; Schmid et al., 1988. Mol. Microbiol., 2: 1–8; Schmid et al., 1991. Mol. Microbiol., 5: 941–950).

Although about 50% of wild-type isolates of *Escherichia coli* are positive for sucrose, the laboratory *E. coli* strains, such as *E. coli* K-12, *E. coli* B, *E. coli* C which are now used for breeding industrially important producing strains, cannot utilize sucrose. However, this property may be easily provided to these strains by introducing sucrose utilization genes from sucrose-positive *E. coli* or *Salmonella* strains using conjugation, transduction, or cloning procedures (Wohlhieter et al., 1975. J. Bacteriol., 122:401–406; Parsell and Smith, 1975. J. Gen. Microbiol., 87: 129–137; Alaeddinoglu and Charles, 1979. J. Gen. Microbiol., 110:47–59; Livshits et al., 1982. In: Metabolic plasmids. P.132–134; Garsia, 1985. Mol. Gen. Genet., 201:575–577; U.S. Pat. No. 5,175,107).

Phosphoenol pyruvate (PEP) is one of the major building blocks in several biosynthetic pathways. PEP is combined with carbon dioxide to produce oxaloacetic acid. Oxaloacetic acid serves as the carbon skeleton for aspartic acid, asparagine, threonine, isoleucine, methionine and lysine. Besides, an equimolar amount PEP is condensed with erythrose-4-phosphate to form 3-deoxy-D-arabino-heptulosonate 7-phosphate (DAHP), which is the first intermediate of the common segment of the aromatic pathway. From this metabolic route, commercially important amino acids such as tryptophan, phenylalanine, and tyrosine can be obtained. The yield of these metabolites may be limited by PEP availability.

During glycolysis four moles of PEP are produced from two moles of glucose, and half of the PEP is obligatorily consumed to provide energy for glucose uptake. In the case of sucrose internalization two moles of hexose (glucose and fructose) arising from one mole of sucrose also produce four moles of PEP, but only one mole is consumed for sucrose transport, thus increasing by 1.5 times the amount of PEP available as a source of carbon skeletons for biosynthesis. Therefore, it is possible to improve the amino acid yield by providing the *E. coli* amino acid producing strains with the ability to utilize sucrose, and using sucrose or sucrose containing substrates as a carbon source.

The threonine producing strain VKPM B-3996 based on *E. coli* K-12 capable of sucrose utilization (U.S. Pat. No. 5,705,371) is known in the present state of the art. The restriction and sequence analysis of the cloned sucrose genes from the VKPM B-3996 strain showed that they are almost identical to those of pUR400 (accession numbers: EMBL X61005; EMBL X67750, GB M38416) encoding PTS sucrose transport and metabolism (Lengeler et al., 1982. J. Bacteriol., 151:468–471; Schmid et al., 1988, Mol. Microbiol., 2:1–8; Schmid et al., 1991, Mol. Microbiol., 5:941–950).

A chromosomally encoded, non-PTS metabolic pathway for sucrose utilization was also found in *Escherichia coli* (Bockmann et al., 1992, Mol. Gen. Genet., 235:22–32). The pathway involves a proton symport transport system (Lac Y type permease), an invertase, a fructokinase, and a sucrose-specific repressor. By using this non-PTS metabolic pathway, the output of an amino acid derived from a PEP precursor could be further increased because sucrose transport into the cells is not coupled to PEP. However, this approach has not been previously used for improving amino acid producing strains.

SUMMARY OF THE INVENTION

It is an object of the present invention to provide a method for producing amino acids using *Escherichia coli* strains containing the genes encoding metabolic pathway for sucrose utilization, especially non-PTS metabolic pathway for sucrose utilization.

The inventors have found that a bacterium belonging to the genus *Escherichia* having amino acid productivity produces the amino acid efficiently by introducing sucrose genes into the bacterium. Thus the present invention has completed.

That is the present invention provides:

A bacterium belonging to the genus *Escherichia* which has been constructed from a sucrose non-assimilative strain belonging to the genus *Escherichia*, the bacterium harboring sucrose PTS genes and having an ability to produce an amino acid other than threonine.

The bacterium as described above, wherein the bacterium belonging to the genus *Escherichia* is *Escherichia coli*.

The bacterium as described above, wherein the amino acid is selected from the group consisting of homoserine, isoleucine, lysine, valine, and tryptophan.

A bacterium belonging to the genus *Escherichia* which has been constructed from a sucrose non-assimilative strain belonging to the genus *Escherichia*, wherein said bacterium harbors sucrose non-PTS genes and has an ability to produce an amino acid.

The bacterium as described above, wherein the sucrose non-PTS genes comprise at least genes coding for a proton symport transport system, invertase, and fructokinase.

A method for producing an amino acid comprising the steps of cultivating the bacterium as described above in a culture medium, and collecting the amino acid from the culture medium.

DESCRIPTION OF THE PREFERRED EMBODIMENTS

Figure 1:
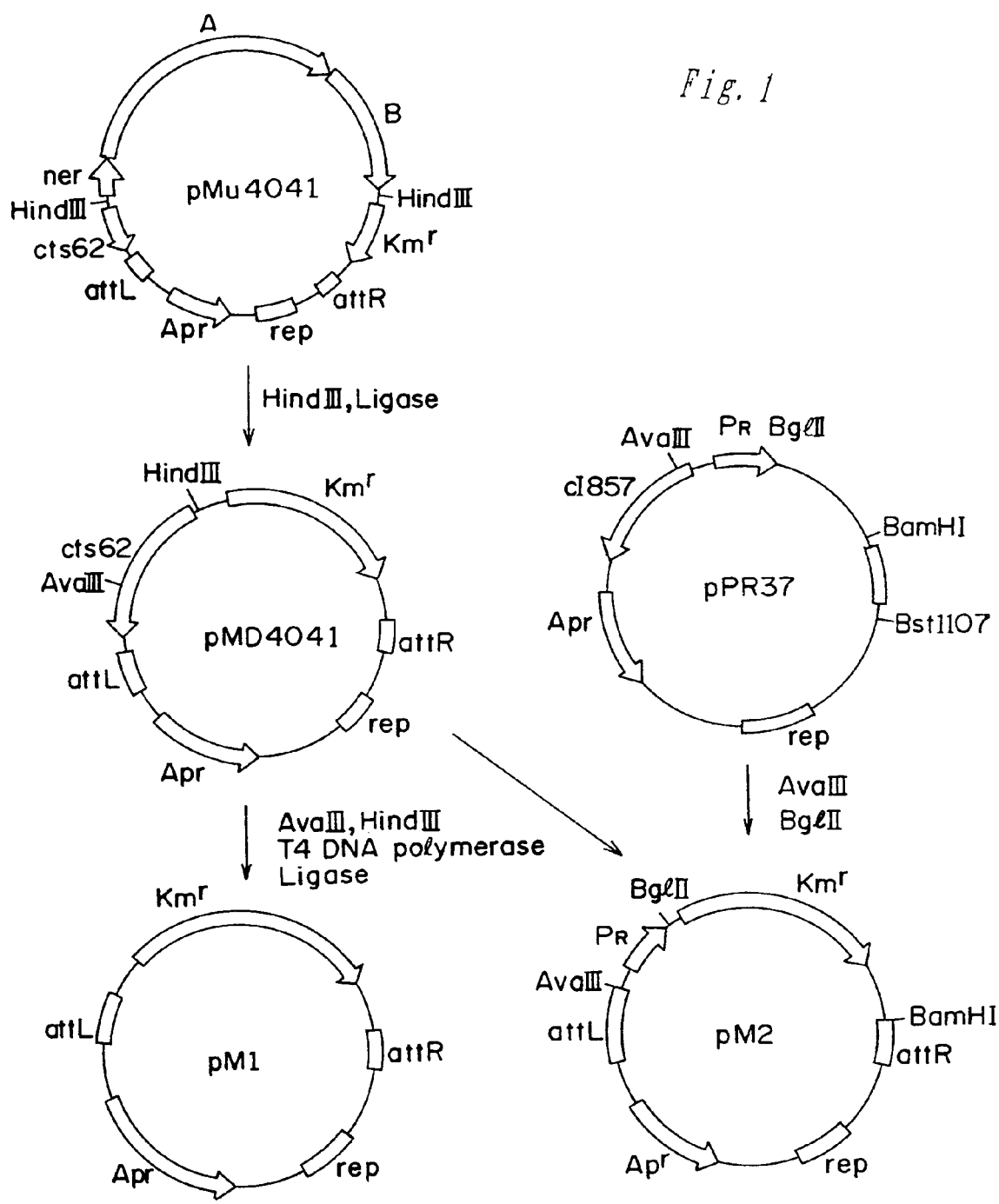
FIG. 1 shows the construction of the plasmids pM1 and pM2, which are derivatives of mini-Mud 4041.

In the present invention, an amino acid is of L-configuration unless otherwise noted.

The present invention will be explained in detail below.

The bacterium belonging to the genus *Escherichia* of the present invention is a strain which is constructed from a sucrose non-assimilative *Escherichia coli* as a parent strain, and which harbors sucrose genes, especially sucrose non-PTS genes, and has an ability to produce an amino acid.

A sucrose non-assimilative *Escherichia coli* is not particularly limited so long as it has an ability to produce an amino acid or such ability can be conferred to it. Examples of such strains include *E. coli* K-12, *E. coli* B and *E. coli* C, and derivatives thereof. More specifically, the amino acid producing strains mentioned herein are encompassed by the present invention.

The bacterium of the present invention may be obtained by introducing sucrose PTS genes or sucrose non-PTS genes into an amino acid producing strain, such as the above-described strains. Alternatively, the bacterium of the present invention may be obtained by conferring an ability to produce an amino acid to a bacterium belonging to the genus *Escherichia* into which sucrose PTS genes or sucrose non-PTS genes are introduced.

Sucrose non-PTS genes are not particularly limited so long as they can function in a bacterium belonging to the genus *Escherichia*. The genes, for example, the sucrose non-PTS genes (csc) harbored by *E. coli* EC3132 (Bockmann et al., 1992. Mol. Gen. Genet., 235:22–32) are encompassed by the present invention. The csc genes may be prepared from *E. coli* K-12 W3350csc. The strain W3350csc has been deposited in Russian National Collection of Industrial Microorganisms (Russia 113545 Moscow 1 Dorozhny proezd, 1) under the provisions of the Budapest Treaty under accession number VKPM B-7914.

The csc genes include the genes coding for a proton symport transport system (Lac Y type permease), invertase, fructokinase, and sucrose-specific repressor. Among these, the present invention requires at least the genes coding for permease, invertase, and fructokinase.

An amino acid can also be efficiently produced by introducing sucrose PTS genes into a bacterium belonging to the genus *Escherichia*. The sucrose PTS genes may be exemplified by scr genes which are included in the pUR400 system encoded by the plasmid derived from the enteric bacterium (Aulkemeyer et al. (1991) Mol. Microbiol., 5: 2913–2922; Schmid et al., 1988, Mol. Microbiol., 2:1–8; Schmid et al., 1991, Mol. Microbiol., 5:941–950). Alternatively, the sucrose PTS genes may be prepared from the transposon Tn2555 (Doroshenko et al., 1988, Molec. Biol., 22:645–658).

The sucrose non-PTS genes and PTS genes can be incorporated into a bacterium belonging to the genus *Escherichia* by, for example, introducing a recombinant plasmid containing the desired genes into the bacterium. Specifically, the desired genes can be incorporated into a bacterium belonging to the genus *Escherichia* by introducing a plasmid, a phage, or a transposon (Berg, D. E. and Berg, C. M., Bio/Tecnol., 1, 417 (1983)) which carries the desired genes into a bacterial cell.

The vector is exemplified by plasmid vectors such as pBR322, pMW118, pUC19, or the like, and phage vectors including $P_1$vir phage, mini-Mud such as pMu4041, or the like. The transposon is exemplified by Mu, Tn10, Tn5, or the like.

The introduction of a DNA into a bacterium belonging to the genus *Escherichia* can be performed, for example, by a method of D. A. Morrison (Methods in Enzymology 68, 326 (1979)) or a method in which recipient bacterial cells are treated with calcium chloride to increase permeability of DNA (Mandel, M. and Higa, A., J. Mol. Biol., 53, 159 (1970)) and the like. Alternatively, introduction of DNA can also be performed by transduction using a phage vector.

The sucrose non-PTS genes or PTS genes are introduced into an amino acid producing bacterium belonging to the genus *Escherichia* with the result that the amino acid is produced from sucrose. As the bacterium belonging to the genus *Escherichia* into which the sucrose non-PTS genes or PTS genes are introduced, strains which produce a desired amino acid may be used. Alternatively, amino acid productivity may be conferred to a bacterium into which the sucrose non-PTS genes or PTS genes are introduced. Examples of amino acid producing bacteria belonging to the genus *Escherichia* are described below.

(1) Threonine Producing Bacteria

As threonine producing bacteria belonging to the genus *Escherichia*, MG442 (referred to Gusyatiner et al., Genetika (in Russian), 14, 947–956 (1978)), VL643, and VL2055 can be exemplified (see Examples 2 and 3).

(2) Homoserine Producing Bacteria

*E. coli* NZ10 and NZ10rhtA23/pAL4 may be exemplified as homoserine producing bacteria belonging to the genus *Escherichia*. The strain NZ10 was obtained as a $Leu^+$ revertant of known strain C600 (Appleyard R. K., Genetics, 39, 440–452 (1954)). The strain NZ10rhtA23/pAL4 was constructed from NZ10 (see Example 4).

(3) Isoleucine Producing Bacteria

As isoleucine producing bacteria, *E. coli* 44-3-15 strain, KX141 strain (VKPM B-4781) (EP-A-519113), and TDH-6/pVIC40, pMWD5 (WO97/08333) may be exemplified.

(4) Lysine Producing Bacteria

As lysine producing bacteria, *E. coli* VL612 is preferable (Example 5). Additionally, there may be exemplified lysine producing bacteria belonging to the genus *Escherichia*. More specifically, a mutant strain having resistance to lysine analogues may be exemplified. The lysine analogues include one which inhibits proliferation of bacteria belonging to the genus *Escherichia*, but the suppression is entirely or partially desensitized if lysine coexists in the medium. For example, oxalysine, lysine hydroxamate, (S)-2-aminoethyl-L-cysteine (AEC), gamma-methyllysine, chlorocaprolactam, and the like may be used. Mutant strains having resistance to these lysine analogues are obtained by applying an ordinary artificial mutation operation to bacteria belonging to the genus Escherichia. The bacterial strain to be used for lysine production is more specifically exemplified by Escherichia coli AJ11442 (deposited as FERM BP-1543 and NRRL B-12185; see Japanese Patent Laid-open No. 56-18596 or U.S. Pat. No. 4,346,170) and Escherichia coli VL611. Escherichia coli AJ11442 was deposited in National Institute of Bioscience and Human Technology, Agency of Industrial Science and Technology (currently National Institute of Bioscience and Human Technology, National Institute of Advanced Industrial Science and Technology) (postal code: 305, 13, Higashi 1 chome, Tsukubashi, Ibarakiken, Japan) on May 5, 1981 under deposit number FERM P-5084, and converted to an international deposit under the provisions of the Budapest Treaty on Oct. 29, 1987, and granted deposit number FERM BP-1543. In aspartokinase of the microorganisms described above, feedback inhibition by lysine is desensitized.

For example, threonine producing bacteria are exemplified, because inhibition of their aspartokinase by lysine is generally desensitized also in the threonine producing microorganisms. As a threonine producing bacterium belonging to E. coli, MG442 (Gusyatiner, et al., Genetika (in Russian), 14, 947–956 (1978) is exemplified.

Gene(s) encoding the enzyme(s) in the lysine biosynthesis may be enhanced in the above-mentioned bacterium. For example, such a gene is exemplified by the gene encoding phosphoenolpyruvate carboxylase which is mutated so that it is desensitized to the feedback inhibition by aspartic acid (see Japanese Patent Publication No. 7-83714).

(5) Valine Producing Bacteria

Valine producing bacteria are more specifically exemplified by E. coli VL 1970 (VKPM B-4411) (see EP-A-519113) and VL1971 (see Example 6). Besides, bacteria belonging to the genus Escherichia which carry the genes for the biosynthesis of valine which have the regulatory mechanism substantially suppressed are exemplified. Such bacteria may be obtained by introducing the ilvGMEDA operon, which does not preferably express threonine deaminase and of which attenuation is suppressed, into bacteria belonging to the genus Escherichia (Japanese Patent Laid-Open Publication No. 8-47397).

The ilvGMEDA operon can be obtained from E. coli chromosomal DNA by colony hybridization or PCR using an oligonucleotide which is prepared according to the nucleotide sequence of the operon. The entire sequence of the operon is disclosed (Nucleic Acid Res., 15, 2137 (1987)). Introduction of a DNA fragment including the ilvGMEDA operon can be performed by a method using a plasmid, phage, or transposon as described above.

(6) Tryptophan Producing Bacteria

A tryptophan producing bacterium is more specifically exemplified by E. coli SV164 (pGH5) (see Example 7), AGX17 (pGX44) (NRRL B-12263), and AGX6 (pGX50) aroP (NRRL B-12264) (U.S. Pat. No. 4,371,614), AGX17/pGX50, pACKG4-pps (WO97/08333).

(7) Phenylalanine Producing Bacteria

A phenylalanine producing bacterium is exemplified by E. coli AJ 12604 (FERM BP-3579) (EP-A-488424).

An amino acid can be efficiently produced from sucrose by cultivating the bacterium described above, into which the sucrose non-PTS genes or PTS genes have been introduced, and which has an ability to produce an amino acid, in a culture medium containing sucrose, to produce and accumulate the amino acid in the medium, and collecting the amino acid from the medium. The amino acid is exemplified preferably by threonine, homoserine, isoleucine, lysine, valine, tryptophan, tyrosine, phenylalanine, and methionine, more preferably by threonine, homoserine, isoleucine, lysine, valine, tryptophan.

In the method for producing amino acids of present invention, the cultivation of the bacterium belonging to the genus Escherichia, the collection and purification of amino acid from the liquid medium may be performed in a manner similar to the conventional fermentation method wherein an amino acid is produced using a bacterium. A medium used in culture may be either a synthetic or a natural medium, so long as the medium includes a carbon and a nitrogen source and minerals and, if necessary, a moderate amount of nutrients which the bacterium used requires for growth. Sucrose is used as the main carbon source. A small amount of carbon from sources other than sucrose may be in the medium as an auxiliary carbon source. As the nitrogen source, various ammonium salts such as ammonia and ammonium sulfate, other nitrogen compounds such as amines, a natural nitrogen source such as a peptone, soybean hydrolyte, and a digested fermentative microbe are used. As minerals, potassium phosphate, magnesium sulfate, sodium chloride, ferrous sulfate, manganese sulfate, calcium carbonate, are used.

The cultivation is performed preferably under aerobic conditions such as a shaking culture, and an aeration and stirring culture, at a temperature of 20–40° C., preferably between 30° C. and 38° C. The pH of the culture is usually between 5 and 9, preferably between 6.5 and 7.2. The pH of the culture can be adjusted with ammonia, calcium carbonate, various acids, various bases, and buffers. Usually, a 1 to 3 day cultivation leads to the accumulation of the target amino acid in the liquid medium.

After cultivation, solids such as cells are removed from the liquid medium by centrifugation and membrane filtration, and then the target amino acid can be collected and purified by ion-exchange, concentration, and crystalline fraction methods.

Hereafter, the present invention will be further specifically explained with reference to the following examples.

EXAMPLE 1

Preparation of the Donor of the Sucrose Non-PTS Genes and PTS Genes (1) Sucrose PTS Genes The strain VD1 was used as a donor of PTS sucrose utilization (scr) genes. This strain was obtained as follows. The transposon Tn2555 carries the scr genes (Doroshenko et al., 1988. Molec. Biol., 22:645–658). The restriction analysis and partial sequencing revealed that the scr genes of Tn2555 are identical to those of pUR400 (accession numbers: EMBL X61005; EMBL X67750, GB M38416) that control sucrose transport and metabolism via the PTS system.

The scr genes of Tn2555 were cloned into pM1, a mini-Mud vector pMu4041 derivative, obtained by the deletion of Mu-phage genes encoding a transposase and a repressor (M. Faelen. Useful Mu and mini-Mu derivatives. In: Phage Mu. Symonds et al., eds. Cold Spring Harbor Laboratory, New York, 1987, pp. 309–316). This was performed in two steps. First, the SspI fragment of pBRS5.2 (pBR325::Tn2555) (Doroshenko et al., 1988. Molec. Biol.

22: 645–658) containing the scrYABR genes and only a part of the scrK gene was inserted into the PvuII-restricted pM1 replacing the kan gene.

The above plasmid pM1 was obtained as follows (FIG. 1). The plasmid pMu4041 was digested with HindIII and re-circularized to excise genes A, B encoding transposase of phage Mu, and the ner gene encoding negative regulator, and the plasmid pMD4041 was obtained. Then pMD4041 was digested with AvaIII and HindIII, and blunt-ended with T4 DNA polymerase followed by recircularization to remove the cts62 phage Mu repressor.

Figure 2:
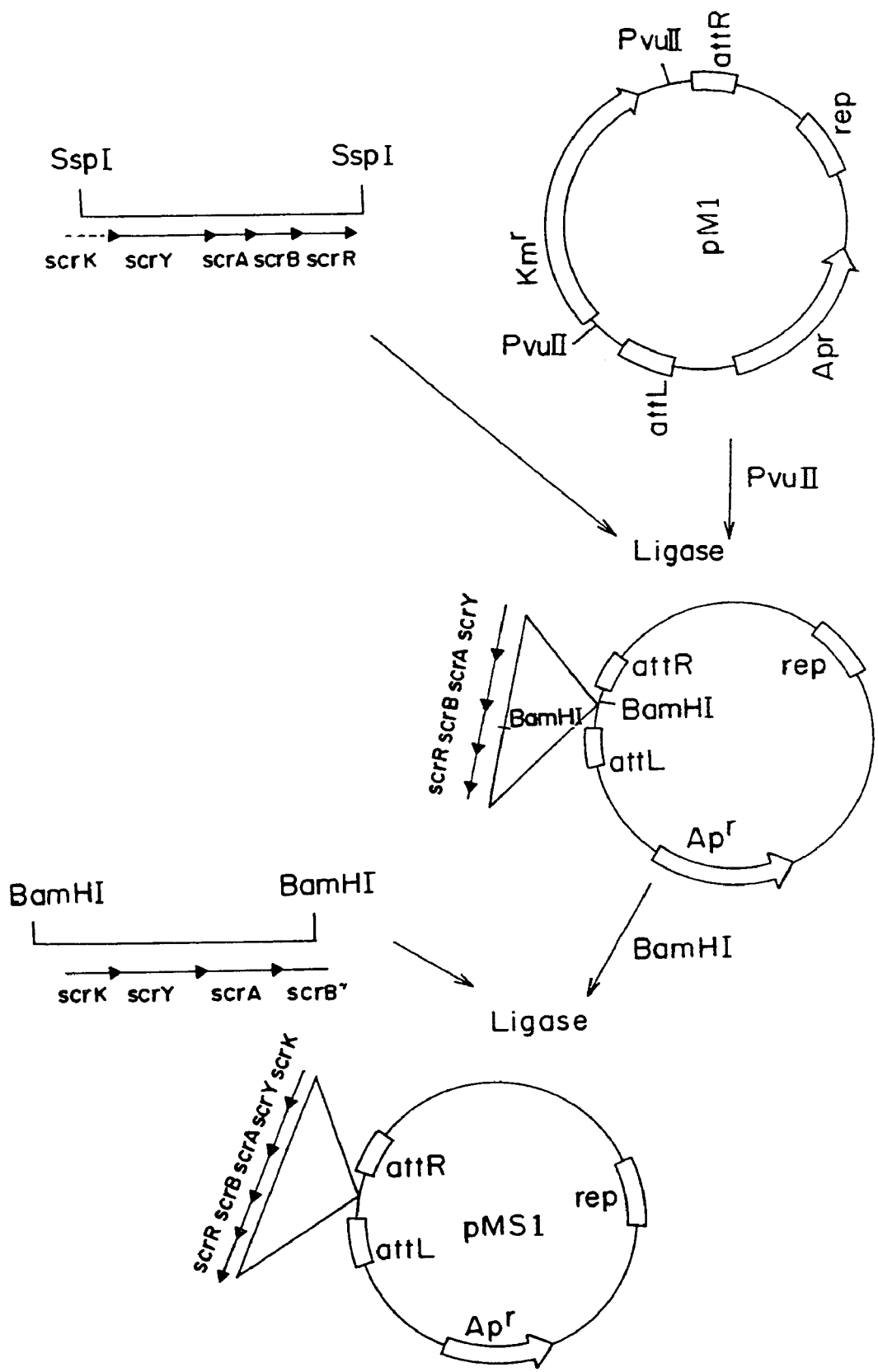
FIG. 2 shows the scheme for cloning the scr genes into pM1.

Next, a BamHI fragment in the resulting plasmid was substituted for the BamHI fragment of pBRS5.2, restoring the scrK gene. Thus the whole sucrose cluster of Tn2555 was cloned into the plasmid also containing the amp$^R$ marker and phage Mu ends. This plasmid, marked as pMS1, contains a transposable mini-Mu-scrKYABR DNA fragment (FIG. 2).

To integrate the mini-Mu-scrKYABR into the bacterial chromosome, a standard procedure was used. pMS1 was introduced into the cells of MG1655 (pMH10). Mu transposase encoded by pMH10 (pACYC177 derivative harboring Km$^R$ gene, Mu-phage A and B genes encoding Mu transposase, cts62 gene encoding Mu repressor, and the phage-lambda repressor gene cI857) was induced by 15 min incubation at 42° C. immediately after transformation. Sucrose-positive (Scr$^+$) clones were selected on M9 agar plates containing 0.2% sucrose as a sole carbon source at 30° C., washed out and incubated in LB-broth (J. Miller. Experiments in molecular genetics. Cold Spring Harbor laboratory, New York, 1972) containing no antibiotics for 48–72 h. Then the appropriate dilutions of the culture broth were plated on M9 agar plates containing 0.2% sucrose. Several tens of Amp$^S$, Km$^S$ clones were picked up and tested. It proved that they did not contain plasmids. Among them, the strain VD1 (MG1655::mini-Mu-scrKYABR) was selected which is a prototrophic fast-growing sucrose-positive strain.

The strain VL478, harboring the pVG478 plasmid containing sucrose genes in the Tn2555 transposon (Molecular Genetics, Microbiology and Virology, No. 6, 23–28 (1987)), was also used as a donor of scr genes. Strain VL478 has been deposited in the Russian National Collection of Industrial Microorganisms (VKPM) under the accession number VKPM B-7915.

The above strains were used as donors of scr genes in the following Examples.

(2) Sucrose Non-PTS Genes

As a source of non-PTS sucrose utilization (csc) genes, the strain of *E. coli* K12 W3350csc was used. This strain contains csc genes of *E. coli* EC3132 (Bockmann et al., 1992. Mol. Gen. Genet., 235:22–32). Strain W3350csc has been deposited in the Russian National Collection of Industrial Microorganisms (VKPM) under the accession number VKPM B-7914. The csc genes contain genes coding for permease, fructokinase, invertase, and repressor.

EXAMPLE 2

Preparation of the *E. coli* Threonine-Producing Strain Capable of Utilizing Sucrose and Threonine Production Using the Strain (1)

As a recipient strain into which the PTS genes were introduced, *E. coli* VL643 was newly constructed as follows.

The known strain *E. coli* MG442 (Gusyatiner et al., Genetika (in Russian), 14, 947–956 (1978), VKPM B-1628) was transduced the rhtA23 mutation from the strain 472T23/pYN7 (VKPM B-2307) to obtain VL643 strain. The rhtA23 is a mutation which confers resistance to high concentrations of threonine (>40 mg/ml) or homoserine (>5 mg/ml), and improves threonine production (ABSTRACTS of 17.sup.th International Congress of Biochemistry and Molecular Biology in conjugation with 1997 Annual Meeting of the American Society for Biochemistry and Molecular Biology, San Francisco, Calif. Aug. 24–29, 1997, abstract No. 457).

The thus obtained threonine-producing strain VL643 was infected with phage P1$_{vir}$ grown on the donor strain VL478. The transductants were selected on M9 minimal medium containing 0.2% sucrose as the sole carbon source. Thus the strain VL644 was obtained. This strain and the parent strain were each cultivated at 37° C. for 18 hours in a nutrient broth, and 0.3 ml of each of the obtained cultures was inoculated into 3 ml of a fermentation medium having the following composition in a 20×200 mm test tube, and cultivated at 37° C. for 72 hours with a rotary shaker.

Fermentation medium composition (g/L):

| | |
|---|---|
| Sucrose (or Glucose) | 50.0 |
| (NH$_4$)$_2$SO$_4$ | 10.0 |
| K$_2$HPO$_4$ | 1.0 |
| NaCl | 1.0 |
| MgSO$_4$*7H$_2$O | 0.8 |
| FeSO$_4$*7H$_2$O | 0.02 |
| MnSO$_4$*5H$_2$O | 0.02 |
| Thiamine hydrochloride | 0.002 |
| CaCO$_3$ | 20 |

(MgSO$_4$*7H$_2$O and CaCO$_3$ were each sterilized separately).

After the cultivation, the amount of threonine which had accumulated in the medium and the absorbance at 560 nm of the medium were determined by known methods. The results are presented in Table 1.

TABLE 1

| | Glucose | | | Sucrose | | |
|---|---|---|---|---|---|---|
| Strain | OD$_{560}$ | Threonine (g/l) | Yield (%) | OD$_{560}$ | Threonine (g/l) | Yield (%) |
| VL643 | 10.1 | 7.0 | 14.0 | — | — | — |
| VL644 | 9.9 | 7.2 | 14.4 | 10.5 | 9.7 | 19.4 |

As shown in Table 1, both strains VL643 and VL644 grew equally well in medium with glucose and were able to cause accumulation of about the same amount of threonine. Besides, the strain VL644 grew well in a medium with sucrose and was able to cause accumulation of more threonine with a higher yield under this condition.

EXAMPLE 3

Preparation of the *E. coli* Threonine-Producing Strain Capable of Utilizing Sucrose and Threonine Production Using the Strain (2)

As a recipient strain into which the PTS genes were introduced, *E. coli* VL2055 was constructed.

*E. coli* VL2055 was derived from the known *E. coli* strain VKPM B-3996 (U.S. Pat. No. 5,705,371). The strain B-3996, of which host strain is *E. coli* TDH-6, is deficient in thrC gene and is sucrose-assimilative, and in which the ilvA gene has a leaky mutation. The strain B-3996 harbors the plasmid pVIC40 which was obtained by inserting the thrA*BC operon including the thrA* gene encoding AKI-HDI which substantially desensitized inhibition by threonine into the RSF1010-derived vector.

From the strain B-3996, VL2055 was constructed by the following two steps.

Initially the plasmidless derivative of the strain VKPM B-3996, TDH-6, was selected after spontaneous elimination of pVIC40 plasmid. Next, a mutation inactivating the kan gene of the Tn5 transposon inserted into the tdh gene of TDH-6 was obtained by a known method (NTG mutagenesis). Then sucrose non-utilizing derivative of the resulting strain was selected after elimination of genetic determinants of sucrose assimilation. Thus the strain VL2053 was obtained.

Figure 3:
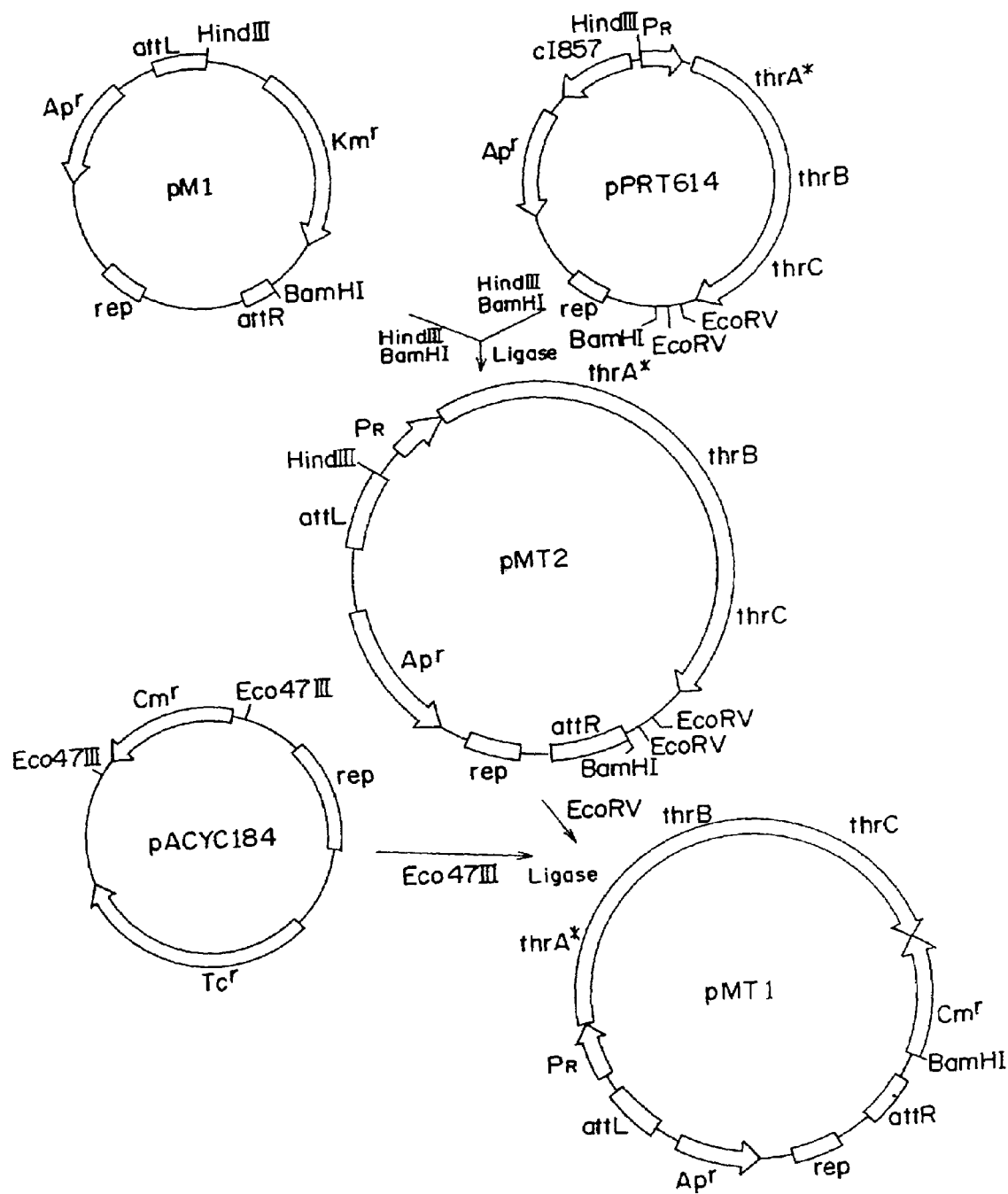
FIG. 3 shows the construction of the plasmids pMT1 and pMT2.

On the other hand, the plasmid pPRT614 (EP 0593792) which is harbored by E. coli VKPM B-5318 was digested with HindIII and BamHI to excise the fragment containing the threonine operon under the lambda-phage $P_R$ promoter. The threonine operon contains a mutation in thrA gene (thrA*), which confers aspartokinase-homoserine dehydrogenase I insensitivity to feedback inhibition by threonine. The obtained fragment was cloned into pM1, a mini-Mud vector pMu4041 derivative (M. Faelen. Useful Mu and mini-Mu derivatives. In: Phage Mu. Symonds et al., eds. Cold Spring Harbor Laboratory, New York, 1987, pp. 309–316) to obtain the plasmid pMT2 (FIG. 3).

In addition, the cat gene of Tn9 from pACYC184 conferring the resistance to chloramphenicol was cloned into pMT2. Thus the plasmid pMT1 containing a transposable construct of $P_R$-thrA*BC and cat genes flanked by Mu ends (mini-Mu-thrA*BC-cat) was obtained (FIG. 3).

Figure 4:
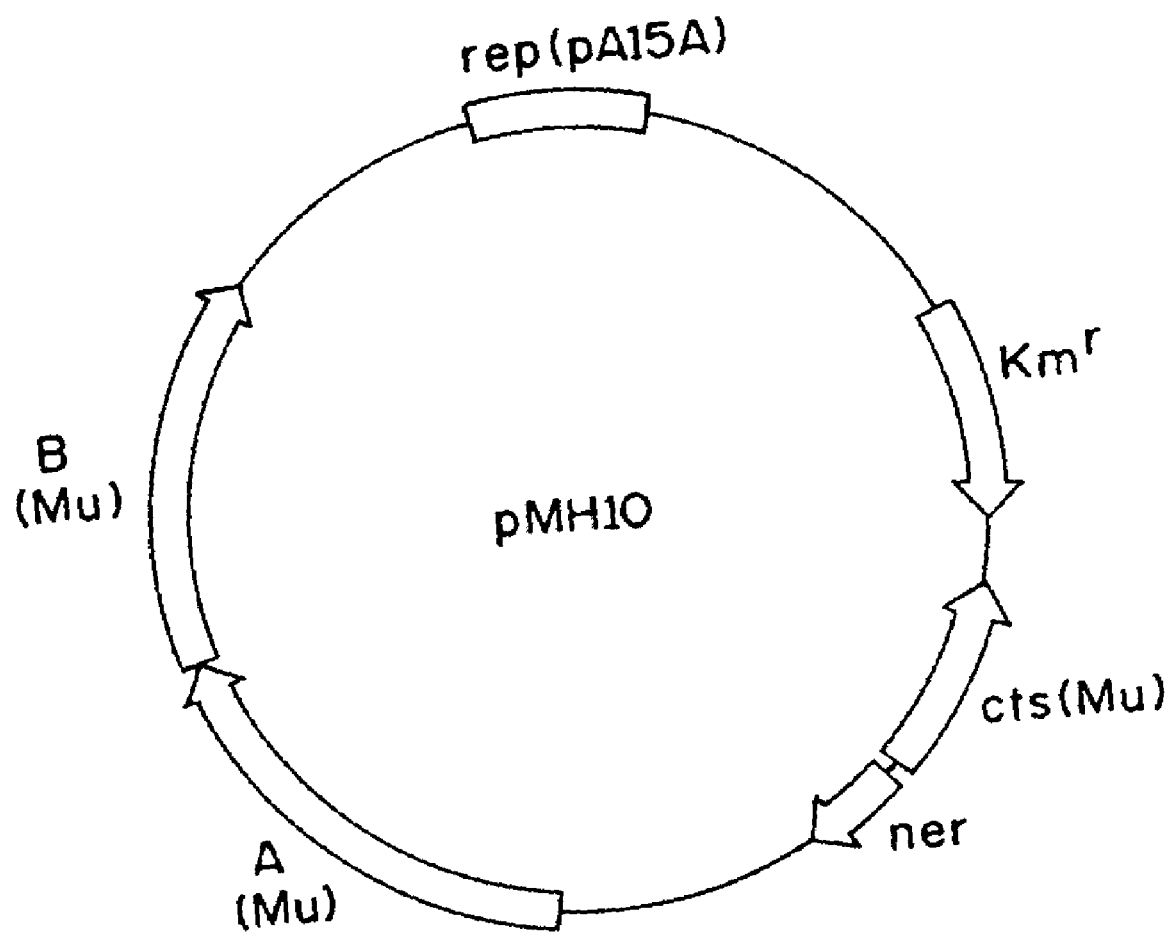
FIG. 4 shows the conformation of the plasmid pMH10 which harbors $Km^R$ gene, Mu-phage A and B genes encoding the Mu transposase, the ner gene encoding the negative regulator, and cts62 gene encoding the Mu repressor.

This plasmid was introduced into the cells of E. coli C600 (pMH10). Mu transposase encoded by pMH10 (pACYC177 derivative harboring $Km^R$ gene, Mu-phage A and B genes encoding Mu transposase, the ner gene encoding negative regulator, and cts62 gene encoding Mu repressor, see FIG. 4) was induced by 15 min incubation at 42° C. immediately after the transformation.

Chloramphenicol resistant ($Cm^R$) clones were selected on LB agar plates containing 15 mg/l chloramphenicol at 30° C. Several tens of $Km^S$ clones were picked up and tested. It proved that most of them did not contain plasmids. Then the $P_R$-thrA*BC-cat genes from the chromosome of one of the selected C600 $Thr^+$, $Cm^R$ strain were transduced by the use of $P1_{vir}$ into the strain VL2053, obtained at the first step, giving the new plasmidless threonine producing strain VL2055.

The threonine-producing strain VL2055 was infected with phage $P1_{vir}$ grown on the donor strains VD1 or W3350csc. The transductants were selected on M9 minimal medium containing 50 mg/l isoleucine and 0.2% sucrose as the sole carbon source. Thus the strains VL2055 Scr and VL2055 Csc, respectively, were obtained. These strains and the parent strain were each cultivated at 37° C. for 18 hours in a nutrient broth, and 0.3 ml of the obtained culture was inoculated into 3 ml of a fermentation medium having the following composition in a 20×200 mm test tube, and cultivated at 37° C. for 72 hours on a rotary shaker.

Fermentation medium composition (g/L):

| | |
|---|---|
| Sucrose (or Glucose) | 80 |
| Isoleucine | 0.1 |
| (NH₄)₂SO₄ | 22 |
| K₂HPO₄ | 2 |
| NaCl | 0.8 |
| MgSO₄*7H₂O | 0.8 |
| FeSO₄*7H₂O | 0.02 |
| MnSO₄*5H₂O | 0.02 |
| Thiamine hydrochloride | 0.2 |
| Yeast Extract | 1.0 |
| CaCO₃ | 30 |

(MgSO₄*7H₂O and CaCO₃ each were sterilized separately)

After the cultivation, the amount of threonine which had accumulated in the medium and an absorbance at 560 nm of the medium were determined by known methods. The results are presented in Table 2.

TABLE 2

| | Glucose | | | Sucrose | | |
|---|---|---|---|---|---|---|
| Strain | $OD_{560}$ | Threonine (g/l) | Yield (%) | $OD_{560}$ | Threonine (g/l) | Yield (%) |
| VL2055 | 12.0 | 18.9 | 23.6 | — | — | — |
| VL2055 scr | 11.7 | 19.5 | 24.4 | 11.4 | 23.3 | 29.1 |
| VL2055 csc | 11.6 | 19.2 | 24.0 | 11.6 | 27.9 | 34.9 |

As shown in Table 2, both sucrose utilizing strains, VL2055 Scr and VL2055 Csc, had the same growth characteristics and were able to cause accumulation of about. the same amount of threonine as their parent VL2055 when cultured in a glucose-containing medium. However, these strains were able to cause accumulation of more threonine with a higher yield when cultured in sucrose-containing medium. Besides, the VL2055 Csc strain (having sucrose non-PTS genes) was more productive under this condition than the VL2055 Scr strain (having sucrose PTS genes).

EXAMPLE 4

Preparation of the E. coli homoserine Producing Strain Capable of Utilizing Sucrose, and Homoserine Production Using this Strain As a recipient strain producing homoserine to which the PTS genes were introduced, E. coli NZ10 rhtA23/pAL4 was constructed by derivation from the strain NZ10. The strain NZ10 (thrB) is a $leuB^+$-revertant obtained from the E. coli strain C600 (thrB, leuB) (Appleyard R. K., Genetics, 39, 440–452 (1954)). Then the rhtA23 mutation was introduced as described in Example 2, giving the NZ10 rhtA23 strain. This strain was transformed with the pAL4 plasmid which was a pBR322 vector into which the thrA gene coding for aspartokinase-homoserine dehydrogenase I was inserted.

The homoserine-producing strain NZ10 rhtA23/pAL4 was infected with the phage $P1_{vir}$ grown on the donor strain VD1. The transductants were selected on M9 minimal medium containing 0.2% sucrose and 50 mg/l threonine. Thus the strain NZ10 rhtA23 scr/pAL4 was obtained. This strain and the parent strain were each cultivated at 37° C. for 18 hours in a nutrient broth, and 0.3 ml of the obtained culture was inoculated. into 3 ml of a fermentation medium in a 20×200 mm test tube, and cultivated at 37° C. for 48 hours with a rotary shaker. The fermentation medium had the same composition as that described in Example 3, except for 0.2 g/l threonine was added instead of isoleucine.

After the cultivation, the amount of homoserine which had accumulated in the medium and an absorbance at 560 nm of the medium were determined by known methods. The results are presented in Table 3.

TABLE 3

| Strain | Glucose | | | Sucrose | | |
|---|---|---|---|---|---|---|
| | OD$_{560}$ | Homo-serine (g/l) | Yield (%) | OD$_{560}$ | Homoserine (g/l) | Yield (%) |
| NZ10rhtA23/pAL4 | 19.3 | 7.8 | 9.7 | — | — | — |
| NZ10rhtA23 Scr/pAL4 | 20.0 | 8.0 | 10.0 | 21.4 | 12.2 | 15.2 |

As shown in Table 3, the NZ10 rhtA23 scr/pAL4 strain and its parent NZ10 rhtA23/pAL4 grew about equally well and were able to cause accumulation of about the same amount of homoserine when cultured in glucose-containing medium. However, the NZ10 rhtA23 scr/pAL4 strain was able to cause accumulation of more homoserine with a higher yield when cultured in a sucrose-containing medium.

EXAMPLE 5

Preparation of the *E. coli* Isoleucine Producing Strain Capable of Utilizing Sucrose, and Isoleucine Production Using this Strain As the isoleucine-producing bacterium belonging to the genus *Escherichia, E. coli* K-12 strain 44-3-15 was used. This strain was constructed as follows. The wild-type *E. coli* K-12 strain VKPM B-7 was used as a parent. After the sequential procedures of NTG mutagenesis and selection for resistance to valine, 4-aza-DL-leucine and 3-hydroxy-DL-leucine, the strain 44 was obtained which contains at least two mutations in ilvGMEDA operon: a mutation in the ilvG gene (ilvG*) restoring acetohydroxy acid synthase II activity, and a mutation in ilvA gene (ilvA*) conferring threonine deaminase insensitivity to feedback inhibition by isoleucine. This strain can produce some amount of isoleucine.

On the other hand, the plasmid pVR72, a derivative of the pVR4 plasmid (Gavrilova et al., 1988, Biotechnologiya (in Russian), 4: 600–608) harboring the ilvG$_5$MEDA$_{7434}$YC genes, was constructed by the introduction of the BamHI linkers into the DraIII and XmaIII sites. Next, the BamHI fragment of pVR72 containing the ilvG$_5$MEDA$_{7434}$YC genes having a deleted promoter and attenuator was cloned into pM2, a mini-Mud vector pMu4041 derivative containing the P$_R$ promoter of the phage lambda. The resulting plasmid was used for the introduction of the mini-Mu-P$_R$-ilvG*MEDPA*YC construct into the chromosome of the 44 (pMH10) strain as described above. After the Mu transposase induction procedure, the clones were tested for their ability to produce isoleucine. Among them, the most productive strain 44-3 was selected. Finally, the mini-Mu-P$_R$-thrA*BC-cat construct was transduced into the 44-3 strain from C600 Thr$^+$, Cm$^R$ as described above. Thus the strain 44-3-15 was obtained.

The isoleucine-producing strain 44-3-15 was infected with phage P1$_{vir}$ grown on the donor strains VD1 or W3350csc. The transductants were selected on M9 minimal medium containing 0.2% sucrose as the sole carbon source. Thus the strains 44-3-15 Scr and 44-3-15 Csc were obtained.

These strains and the parent strain were each cultivated at 37° C. for 18 hours in a nutrient broth, and 0.3 ml of the obtained culture was inoculated into 3 ml of a fermentation medium in a 20×200 mm test tube, and cultivated at 37° C. for 72 hours on a rotary shaker. The fermentation medium had the same composition as that described in Example 3, except that isoleucine was not added. After the cultivation, the amount of isoleucine which had accumulated in the medium and an absorbance at 560 nm of the medium were determined by known methods. The results are presented in Table 4.

TABLE 4

| Strain | Glucose | | | Sucrose | | |
|---|---|---|---|---|---|---|
| | OD$_{560}$ | Isoleucine (g/l) | Yield (%) | OD$_{560}$ | Isoleucine (g/l) | Yield (%) |
| 44-3-15 | 16.1 | 10.4 | 13.0 | — | — | — |
| 44-3-15 Scr | 16.4 | 10.8 | 13.5 | 16.1 | 13.1 | 16.4 |
| 44-3-15 Csc | 15.3 | 10.5 | 13.1 | 16.0 | 13.6 | 17.0 |

As shown in Table 4, both sucrose utilizing strains, 44-3-15 Scr and 44-3-15 Csc, had the same growth characteristics and were able to cause accumulation of about the same amount of isoleucine as their parent 44-3-15 when cultured in a glucose-containing medium. However, these strains were able to cause accumulation of more isoleucine with a higher yield when cultured in a sucrose-containing medium. Besides, the 44-3-15 Csc strain (having sucrose non-PTS genes) was slightly more productive under this condition than the 44-3-15 Scr strain (having sucrose PTS genes)

EXAMPLE 6

Preparation of the *E. coli* Lysine Producing Strain Capable of Utilizing Sucrose, and Lysine Production Using this Strain As a recipient strain producing lysine *E. Coli* strain, VL612 was used. This strain was obtained from the known *E. coli* strain GiflO2 (Theze, J. and Saint Girons., J. Bacteriol., 118, 990–998, 1974) in the two steps. First, the mutants of the strain resistant to 2 mg/ml S-(2-aminoethyl)-L-cysteine were selected and among them the strain VL611 capable of producing lysine was found. Then, the mutation rhtA23 was introduced into VL611 as above, giving the strain VL612.

The strain VL612 was infected with phage P1$_{vir}$ grown on the donor strain VL478. The transductants were selected on M9 minimal medium containing 50 mg/l homoserine and 0.2% sucrose as the sole carbon source. Thus the strain VL613 (VKPM B-3423) was obtained. This strain and the parent strain were each cultivated at 37° C. for 18 hours in a nutrient broth, and 0.3 ml of the obtained culture was inoculated into 3 ml of a fermentation medium in a 20×200 mm test tube, and cultivated at 37° C. for 72 hours on a rotary shaker. The fermentation medium had the same composition as that described in Example 2, except that 0.2 g/l homoserine was added. After the cultivation, the amount of lysine which had accumulated in the medium and an absorbance at 560 nm of the medium were determined by known methods. The results are presented in Table 5.

TABLE 5

| Strain | Glucose | | | Sucrose | | |
|---|---|---|---|---|---|---|
| | OD$_{560}$ | Lysine (g/l) | Yield (%) | OD$_{560}$ | Lysine (g/l) | Yield (%) |
| VL612 | 11.5 | 2.8 | 5.6 | — | — | — |
| VL613 | 11.2 | 2.7 | 5.4 | 11.4 | 4.2 | 8.4 |

As shown in Table 5, the VL612 strain and the VL613 strain grew about equally well in glucose-containing medium and were able to cause accumulation of about the same amount of lysine. However, the VL613 strain was able to cause accumulation of more lysine with a higher yield when cultured in a sucrose-containing medium.

EXAMPLE 7

Preparation of the E. coli Valine Producing Strain Capable of Utilizing Sucrose, and Valine Production Using this Strain As a valine producing bacterium belonging to the genus Escherichia, E. coli strain VL1971 was used. This strain is a derivative of the known strain VL1970 (VKPM B-4411, U.S. Pat. No. 5,658,766) to which the rhtA23 mutation was introduced, as described in Example 1.

The E. coli strain VL1971 was infected with the phage $P1_{vir}$ grown on the VL478 donor strain and plated to the M9 minimal medium containing 0.2% sucrose as the sole carbon source. The transductants which had grown after 40 h were picked, purified, and among them the valine producing strain, VL1972 (VKPM B-4413), which was capable of utilizing sucrose was selected.

VL1971 and VL1972 were each cultivated at 37° C. for 18 hours in a nutrient broth, and 0.3 ml of the obtained culture was inoculated into 3 ml of a fermentation medium in a 20×200 mm test tube, and cultivated at 37° C. for 72 hours with a rotary shaker. The fermentation medium had the same composition as that described in Example 3. After the cultivation, the amount of valine which had accumulated in the medium and an absorbance at 560 nm of the medium were determined by known methods. The results are shown in Table 6.

TABLE 6

| Strain | Glucose | | | Sucrose | | |
|---|---|---|---|---|---|---|
| | $OD_{560}$ | Valine (g/l) | Yield (%) | $OD_{560}$ | Valine (g/l) | Yield (%) |
| VL1971 | 12.4 | 8.0 | 10.0 | — | — | — |
| VL1972 | 12.6 | 8.2 | 10.2 | 14.4 | 11.2 | 14.0 |

As shown in Table 6, the VL1971 and VL1972 strains grew equally well and were able to cause accumulation of about the same amount of valine when cultured in a glucose-containing medium. However, the VL1972 strain was able to cause accumulation of more valine with a higher yield when cultured in a sucrose-containing medium.

It is worthy to note that PTS sucrose genes confer a higher productivity to the valine producer although phosphoenol pyruvate is not necessary for valine synthesis.

EXAMPLE 8

Preparation of the E. coli Tryptophan Producing Strain Capable of Utilizing Sucrose, and Tryptophan Production Using this Strain As a recipient strain of bacterium belonging to the genus Escherichia, the strain SV164 (pGH5) (WO94/08031) was used.

The tryptophan overproducing strain SV164 (pGH5) was infected with phage $P1_{vir}$ grown on the donor strains VD1 or W3350csc. The transductants were selected on M9 minimal medium containing 50 mg/l tyrosine, 50 mg/ml phenylalanine, 0.2% sucrose as the sole carbon source and 15 mg/l tetracycline. Thus the strains SV164scr (pGH5) and SV164csc (pGH5), respectively, were obtained.

These strains and the parent strain were each cultivated at 29° C. for 18 hours in a nutrient broth, and 0.3 ml of the obtained culture was inoculated into 3 ml of a fermentation medium having the following composition in a 20×200 mm test tube, and cultivated at 29° C. for 40 hours on a rotary shaker.

Fermentation medium composition (g/l):

| | |
|---|---|
| Glucose (or Sucrose) | 40 |
| phenylalanine | 0.1 |
| tyrosine | 0.1 |
| $(NH_4)_2SO_4$ | 15 |
| $KH_2PO_4$ | 1.5 |
| NaCl | 0.5 |
| $MgSO_4 \times 7H_2O$ | 0.3 |
| $CaCl_2 \times 2H_2O$ | 0.015 |
| $FeSO_4 \times 7H_2O$ | 0.075 |
| $Na_3$-citrate | 1 |
| $Na_2MoO_4 \times 2H_2O$ | 0.00015 |
| $H_3BO_3$ | 0.0025 |
| $CoCl_2 \times 6H_2O$ | 0.0007 |
| $CuSO_4 \times 5H_2O$ | 0.00025 |
| $MnCl_2 \times 4H_2O$ | 0.0016 |
| $ZnSO_4 \times 7H_2O$ | 0.0003 |
| Thiamine HCl | 0.005 |
| Pyridoxine | 0.03 |
| Corn Steep Solids (AJINOMOTO) | 2 |
| $CaCO_3$ | 30 |
| Tetracycline | 0.015 |

After the cultivation, the amount of tryptophan which had accumulated in the medium and an absorbance at 560 nm of the medium were determined by known methods. The results are presented in Table 7. As shown in Table 7, both sucrose utilizing strains, SV164scr(pGH5) and SV164csc (pGH5), had nearly the same growth characteristics and were able to cause accumulation of about the same amount of tryptophan as their parent SV164 (pGH5) when cultivated in a glucose-containing medium. However, these strains were able to cause accumulation of more tryptophan with a higher yield when cultivated in a sucrose-containing medium. Moreover, the SV164csc(pGH5) strain (having sucrose non-PTS genes) was more productive under this condition than the strain SV164scr(pGH5) (having sucrose PTS genes).

TABLE 7

| Strain | Glucose | | | Sucrose | | |
|---|---|---|---|---|---|---|
| | $OD_{560}$ | Tryptophan (g/l) | Yield (%) | $OD_{560}$ | Tryptophan (g/l) | Yield (%) |
| SV164 (pGH5) | 6.0 | 5.0 | 12.5 | — | — | — |
| SV164 scr (pGH5) | 6.2 | 5.1 | 12.7 | 6.2 | 5.5 | 13.7 |
| SV164 csc (pGH5) | 6.0 | 5.0 | 12.5 | 6.2 | 5.6 | 14.0 |

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety, including the foreign priority document RU200110350, filed Apr. 26, 2000.

What is claimed is:

1. A method for producing an amino acid selected from the group consisting of isoleucine, lysine, and valine comprising:
   a) cultivating in a culture medium which contains sucrose as a carbon source a bacterium belonging to the genus *Escherichia* which has been constructed from a sucrose non-assimilative strain belonging to the genus *Escherichia*, wherein said bacterium harbors sucrose PTS genes from *Eseherichia coli* VKPM B-7915 and has an ability to produce said amino acid, and
   b) collecting said amino acid from said medium.

2. The method according to claim 1, wherein said bacterium is *Escherichia coli*.

3. The method according to claim 1, wherein said sucrose PTS genes are scrKYABR genes.

* * * * *